United States Patent [19]

Lindner et al.

[11] Patent Number: 4,968,795
[45] Date of Patent: Nov. 6, 1990

[54] SUBSTITUTED 1,2,4-TRIAZINEDIONES, PROCESSES FOR THEIR PREPARATION AND THEIR USE

[75] Inventors: Werner Lindner, Cologne; Axel Haberkorn, Wuppertal, both of Fed. Rep. of Germany

[73] Assignee: Bayer Aktiengesellschaft, Leverkusen, Fed. Rep. of Germany

[21] Appl. No.: 464,089

[22] Filed: Jan. 12, 1990

Related U.S. Application Data

[62] Division of Ser. No. 310,809, Feb. 14, 1989.

[30] Foreign Application Priority Data

Feb. 24, 1988 [DE] Fed. Rep. of Germany ....... 3805660

[51] Int. Cl.$^5$ ............... C07D 253/075; C07C 261/00; C07C 243/16
[52] U.S. Cl. .................... 544/182; 558/391; 560/29
[58] Field of Search .......... 544/182; 560/29; 558/391

[56] References Cited

PUBLICATIONS

J. Slouka Fdc. Rerum Nat. 1984, 79, Chem. 231, 39–45 (Chem Abs., vol. 102, 1985, Ab. 203946k.
Morrison and Boyd, Organic Chemistry (Boston, Allyn and Bacon, 1979), pp. 758–761.
J. Slouka Collect. Czech. Chem. Communications 1977 42(3), 894–901 Chem. Abs., vol. 87, 1977, Abs. 102271c.
J. Slouka Monatsh. 94, 258–262, 1963, Chem. Abs. vol. 59, 1963, Ab. 5166B.

Primary Examiner—Mukund J. Shah
Assistant Examiner—E. C. Ward
Attorney, Agent, or Firm—Sprung Horn Kramer & Woods

[57] ABSTRACT

A substituted 1,2,4-triazinedione of the formula

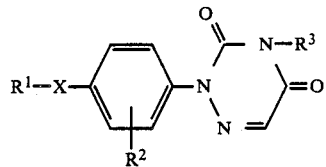

in which $R^1$ stands for an unsubstituted or substituted heteroaromatic radicals bonded via carbon, X stands for one or more, identical or different radicals selected from the group consisting of hydrogen, halogen, nitro, alkyl, alkoxy, alkylthio, halogenoalkyl, halogenoalkoxy and halogenoalkylthio.

$R^3$ stands for hydrogen, unsubstituted or substituted alkyl, alkenyl, alkinyl or aralkyl. The substituted 1,2,4-triazinedione is useful to combat parasitic protozoa in warmblooded animals.

4 Claims, No Drawings

SUBSTITUTED 1,2,4-TRIAZINEDIONES, PROCESSES FOR THEIR PREPARATION AND THEIR USE

This is a division of application Ser. No. 07/310,809, filed 2/14/89, now pending.

The present invention relates to new substituted 1,2,4-triazinediones, processes for their preparation, intermediates for carrying out these processes, and their use.

The use of substituted 1,2,4-triazinediones for combating Coccidia is known. However, the action of these compounds is not satisfactory in all cases.

The present invention relates to
(1) New substituted 1,2,4-triazinediones of the general formula I

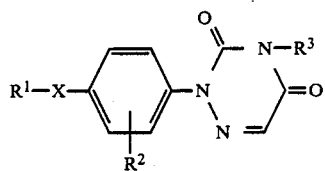

in which
R$^1$ stands for heteroaromatic radicals bonded via carbon which are optionally substituted,
X stands for O, S, SO or SO$_2$,
R$^2$ stands for one or more, identical or different radicals form the group comprising hydrogen, halogen, nitro, alkyl, alkoxy, alkylthio, halogenoalkyl, halogenoalkoxy and halogenoalkylthio,
R$^3$ stands for hydrogen, optionally substituted alkyl, alkenyl, alkinyl or aralkyl.

(2) Processes for the preparation of substituted 1,2,4-triazinediones of the general formula I

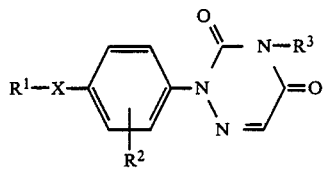

in which
R$^1$ stands for heteroaromatic radicals bonded via carbon which are optionally substituted,
X stands for O, S, SO or SO$_2$,
R$^2$ stands for hydrogen, one or more, identical or different radicals from the group comprising hydrogen, halogen, nitro, alkyl, alkoxy, alkylthio, halogenoalkyl, halogenoalkoxy and halogenoalkylthio,
R$^3$ stands for hydrogen, optionally substituted alkyl, alkenyl, alkinyl or aralkyl,
(a) Compounds of the formula II

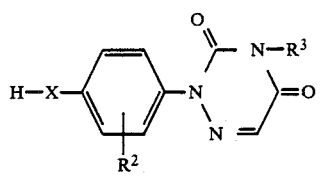

in which
X stands for O or S,
R$^2$ and R$^3$ have the abovementioned meanings are reacted with compounds of the formula III

R$^1$—A            III in which
R$^1$ has the abovementioned meaning and
A stands for the radicals halogen, O—SO$_2$-alkyl, —O—SO$_2$-halogenoalkyl, —O—SO$_2$-aryl, or —S-alkyl, —SO$_2$-alkyl or SO$_2$-halogenoalkyl
or
(b) in that for the preparation of compounds of the formula I in which R$^3$ does not stand for hydrogen, compounds of the formula Ia

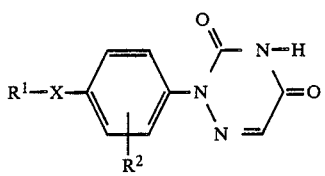

in which
R$^1$, R$^2$, and X have the abovementioned meanings, are reacted with compounds of the formula IV

R$^3$—B            IV in which
R$^3$ stands for optionally substituted alkyl, alkenyl, alkinyl or aralkyl and
B stands for halogen, —O—SO$_2$-alkyl, —O—SO$_2$-aryl or —O—SO$_2$-halogenoalkyl
(c) in that for the preparation of compounds of the formula I in which X stands for —SO— or —SO$_2$—, compounds of the formula I in which X stands for S are reacted with an oxidant.

(3) New compounds of the formula II

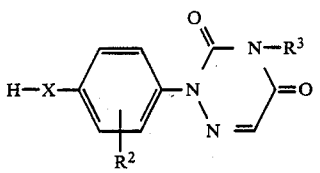

in which
X stands for O or S,
R$^2$ stands for one or more, identical or different radicals from the group comprising halogen, nitro, alkyl, alkoxy, alkythio, halogenoalkyl, halogenoalkoxy and halogenoalkylthio and for the case in which X stands for S, additionally for hydrogen,
R$^3$ stands for hydrogen, alkyl, alkenyl, alkinyl or aralkyl.

(4) Process for the preparation of the new compounds of the formula II according to (3), characterized in that compounds of the formula V

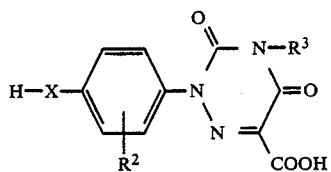

in which
X, $R^2$, $R^3$ have the meanings indicated in (3), are decarboxylated by heating.

(5) New compounds of the formula V

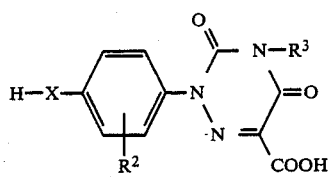

in which
X stands for O or S
$R^2$ stands for one or more, identical or different radicals from the group comprising halogen, nitro, alkyl, alkoxy, alkylthio, halogenoalkyl, halogenoalkoxy and halogenoalkylthio and for the case in which X stands for S, additionally for hydrogen,
$R^3$ stands for hydrogen, alkyl, alkenyl, alkinyl or aralkyl.

(6) Process for the preparation of the new compounds of the formula V according to (5), characterized in that compounds of the formula VI

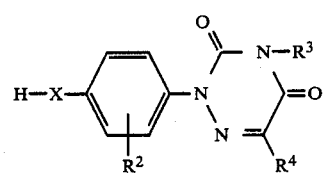

in which
X, $R^2$, $R^3$ have the meanings indicated in (3)
$R^4$ stands for the radicals —CN or

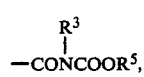

$R^5$ stands for optionally substituted alkyl or aryl are heated in the presence of aqueous acids.

(7) New compounds of the formula VI

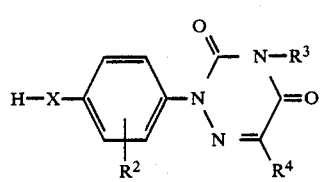

in which
X, $R^2$, $R^3$ and $R^4$ have the meanings indicated in (6).

(8) Process for the preparation of the new compounds of the formula VI according to (7), characterized in that compounds of the formula VII

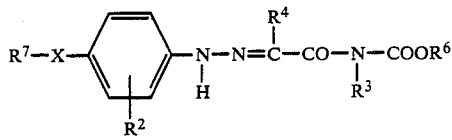

in which
X, $R^2$, $R^3$ and $R^4$ have the meanings indicated in (7) and
$R^6$ stands for alkyl or optionally substituted aryl,
$R^7$ stands for hydrogen or optionally substituted

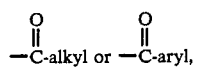

are heated in the presence of bases.

(9) New compounds of the formula VII

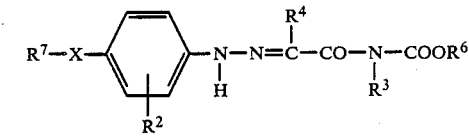

in which
X, $R^2$, $R^3$, $R^4$, $R^6$ and $R^7$ have the meanings indicated in (8) and for the case in which $R^7$ stands for H or X stands for S, $R^2$ can additionally stand for hydrogen.

(10) Process for the preparation of the new compounds of the formula VII according to (9), characterized in that compounds of the formula VIII

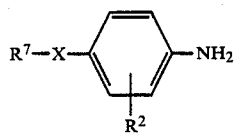

in which
X, $R^2$ and $R^7$ have the meanings indicated in (9), are first diazotized using alkali nitrite in the presence of aqueous mineral acids and then reacted with compounds of the formula IX

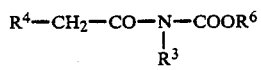

in which
$R^3$, $R^4$ and $R^6$ have the meanings indicated in (9).

The compounds of the formula I and their salts with acids or bases are outstandingly suitable for combating parasitic protozoa.

Preferred compounds of the formula I are compounds in which
$R^1$ stands for thiazolyl, oxazolyl, benzothiazolyl or benzoxazolyl, each of which is optionally substituted by halogen, alkyl, cyano, nitro, o-alkyl, s-alkyl or halogenoalkyl.
X stands for O or S,
$R^2$ stands for halogen or $C_{1-6}$-alkyl and
$R^3$ stands for hydrogen or $C_1$-$C_4$-alkyl, in particular methyl.

Particularly preferred compounds of the formula I are those in which

X stands for O,

R¹ stands for thiazolyl, benzothiazolyl or benzoxazolyl, each of which is optionally substituted by $C_{1-4}$-alkyl, in particular methyl, $C_{1-4}$-halogenoalkyl, in particular trifluoromethyl, halogen, in particular chlorine, bromine or fluorine, nitro, CN, amino, $C_{1-4}$-alkylamino, $C_{1-4}$-halogenoalkylamino, alkylamino, $C_{1-4}$-alkoxy, in particular methoxy, $C_{1-4}$-halogenoalkoxy, in particular trifluoromethoxy, $C_{1-4}$-alkylthio, in particular methylthio and $C_{1-4}$-halogenoalkylthio, in particular trifluoromethylthio, $C_{1-4}$-alkylsulfonyl, in particular methylsulfonyl and $C_{1-4}$-halogenoalkylsulfonyl, in particular trifluoromethylsulfonyl, R² stands for one or more radicals from the group comprising hydrogen or halogen, in particular chlorine, bromine, $C_{1-4}$-alkyl, in particular methyl, and R³ stands for hydrogen.

Very particularly preferred compounds of the formula I are those
in which

X stands for O,

R¹ stands for thiazolyl or benzothiazolyl, each of which is optionally substituted by chlorine or methyl or trifluoromethyl, R² stands for one or more radicals from the group comprising hydrogen, methyl or chlorine, and R³ stands for hydrogen.

Individual compounds which may be mentioned are:

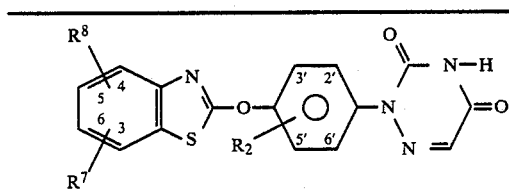

| R₂ | R⁷ | R⁸ |
|---|---|---|
| 3-CH₃ | 6-Cl | H |
| 3-CH₃ | 6-CF₃ | H |
| 3-CH₃ | 5-Cl | 6-Cl |
| 3,5-Cl | 6-Cl | H |
| 3,5-Cl | 6-CF₃ | H |
| 3,5-Cl | 5-Cl | 6-Cl |

The following compounds may furthermore be mentioned:

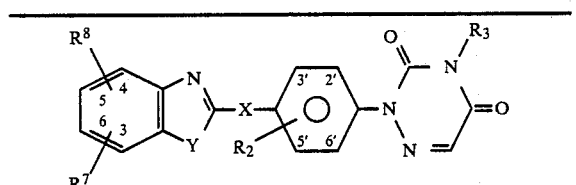

| Y | R₂ | X = O R₃ | R₇ | R₈ |
|---|---|---|---|---|
| S | H | H | H | H |
| S | H | H | 6-Cl | H |
| S | H | H | 6-Br | H |
| S | H | H | 6-F | H |
| S | H | H | 6-CH₃ | H |
| S | H | H | 6-OCH₃ | H |
| S | H | H | 6-NO₂ | H |
| S | H | H | 6-CN | H |
| S | H | H | 6-CF₃ | H |
| S | H | H | 6-SCF₃ | H |
| S | H | H | 6-OCF₃ | H |
| S | H | H | 5-Cl | 6-Cl |
| S | 3'-CH₃ | H | H | H |
| S | 3'-CH₃ | H | 6-Br | H |
| S | 3'-CH₃ | H | 6-F | H |
| S | 3'-CH₃ | H | 6-CH₃ | H |
| S | 3-CH₃ | H | 6-OCH₃ | H |
| S | 3-CH₃ | H | 6-NO₂ | H |
| S | 3-CH₃ | H | 6-CN | H |
| S | 3-CH₃ | H | 6-SCF₃ | H |
| S | 3-Cl | H | H | H |
| S | 3-Cl | H | 6-Cl | H |
| S | 3-Cl | H | 6-Br | H |
| S | 3-Cl | H | 6-F | H |
| S | 3'-Cl | H | 6-CH₃ | H |
| S | 3'-Cl | H | 6-OCH₃ | H |
| S | 3'-Cl | H | 6-NO₂ | H |
| S | 3'-Cl | H | 6-CN | H |
| S | 3'-Cl | H | 6-CF₃ | H |
| S | 3'-Cl | H | 6-SCF₃ | H |
| S | 3'-Cl | H | 6-OCF₃ | H |
| S | 3'-Cl | H | 5-Cl | 6-Cl |
| S | 3',5'-Cl | H | H | H |
| S | 3',5'-Cl | H | 6-Br | H |
| S | 3',5'-Cl | H | 6-CH₃ | H |
| S | 3',5'-Cl | H | 6-OCH₃ | H |
| S | 3',5'-Cl | H | 6-NO₂ | H |
| S | 3',5'-Cl | H | 6-CN | H |
| S | 3',5'-Cl | H | 6-SCF₃ | H |
| S | 3',5'-Cl | H | 6-OCF₃ | H |
| S | 3'-Cl, 5'-CH₃ | H | H | H |
| S | 3'-Cl, 5'-CH₃ | H | 6-Cl | H |
| S | 3'-Cl, 5'-CH₃ | H | 6-Br | H |
| S | 3'-Cl, 5'-CH₃ | H | 6-F | H |
| S | 3'-Cl, 5'-CH₃ | H | 6-OCH₃ | H |
| S | 3'-Cl, 5'-CH₃ | H | 6-CN | H |
| S | 3'-Cl, 5'-CH₃ | H | 6-CN | H |
| S | 3'-Cl, 5'-CH₃ | H | 6-CF₃ | H |
| S | 3'-Cl, 5'-CH₃ | H | 6-SCF₃ | H |
| S | 3'-Cl, 5'-CH₃ | H | 5-Cl | 6-Cl |
| S | 3'-CH₃, 5'-CH₃ | H | 6-Cl | H |
| S | 3'-CH₃, 5'-CH₃ | H | 5-Cl | 6-Cl |
| S | 3'-CH₃, 5-CH₃ | H | 5-Cl | H |
| S | 3'-Cl | H | 5-Cl | H |
| S | 3'-CH₃ | H | 5-Cl | H |
| S | 3'-Cl, 5'-CH₃ | H | 5-Cl | H |
| S | 3'-Cl, 5'-Cl | H | 5-Cl | H |
| S | 3'-Br | H | 6-Cl | H |
| S | 3'-Br, 5'-Br | H | 6-Cl | H |
| S | 3'-CF₃ | H | 6-Cl | H |
| S | 3'-CF₃, 5'-Cl | H | 6-Cl | H |
| O | 3'-Cl, 5'-Cl | H | 6-Cl | H |
| O | 3'-CH₃ | H | 6-Cl | H |
| S | 3'-Cl, 5'-Cl | CH₃ | 6-CL | H |
| S | 3'-CH₃ | —C₂H₅ | 5-Cl | 6-Cl |

| Y | X | R₂ | R₃ | R₇ | R₈ |
|---|---|---|---|---|---|
| S | S | H | H | 6-Cl | H |
| S | S | H | H | H | H |
| O | S | H | H | H | H |
| O | SO | H | H | H | H |
| O | SO₂ | H | H | H | H |
| O | S | 3,5-Cl₂ | H | 6-Cl | H |
| O | S | 3,5-Cl₂ | H | H | H |

| Y | R₂ | R₃ | R₇ | R₈ |
|---|---|---|---|---|
| S | H | H | H | H |
| S | H | H | Cl | H |
| S | H | H | Cl | Cl |
| S | H | H | Cl | CF₃ |
| S | H | H | Cl | CH₃ |

| | | | | |
|---|---|---|---|---|
| S | 3'-Cl | H | H | H |
| S | 3'-Cl | H | Cl | H |
| S | 3'-Cl | H | Cl | Cl |
| S | 3'-Cl | H | Cl | CF$_3$ |
| S | 3'-CH$_3$ | H | Cl | H |
| S | 3'-CH$_3$ | H | Cl | Cl |
| S | 3'-CH$_3$ | H | Cl | CF$_3$ |
| S | 3'-Cl, 5'-Cl | H | Cl | H |
| S | 3'-Cl, 5'-Cl | H | Cl | Cl |
| S | 3'-Cl, 5'-Cl | H | Cl | CF$_3$ |
| O | 3'-Cl, 5'-Cl | H | H | H |
| O | 3'-CH$_3$ | H | H | H |
| O | 3'-Cl, 5'-Cl | H | Cl | H |
| O | 3'-CH$_3$ | H | Cl | H |
| S | 3'-Cl, 5'-Cl | CH$_3$ | Cl | Cl |
| S | 3'-CH$_3$ | C$_2$H$_5$ | Cl | Cl |

If 2-(3,5-dichloro-4-hydroxyphenyl)-1,2,4-triazine-3,5(2H,4H)dione is used as the compound II and 2,6-dichlorobenzothiazole is used as the compound of the formula III in process 2, the process can be described by the following equation:

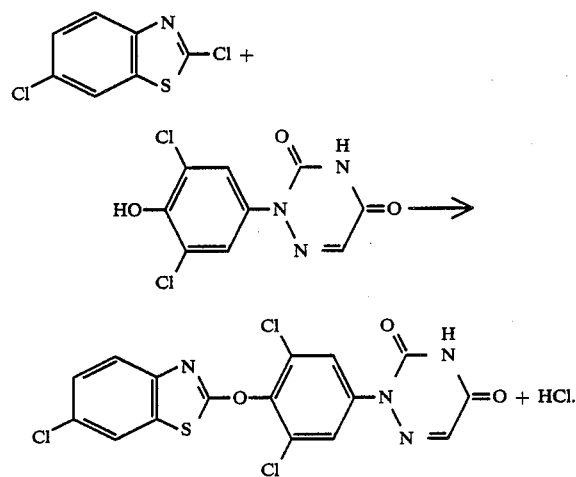

Compounds of the formula II
in which
R$^2$ and R$^3$ stand for hydrogen are known (J. Slouka, Acta Unio Palacki Olomuk. Fac. Rerum. Nat. 1984 (Chem 23), 39–45; C.A. 102 203946c).

Compounds of the formula II in which R$^2$ stands for radicals other than hydrogen are new.

Preferably, compounds of the formula II may be mentioned in which R$^2$ and R$^3$ have the meanings mentioned as preferred in the compounds of the formula I.

The following new compounds of the formula II may be mentioned in detail.

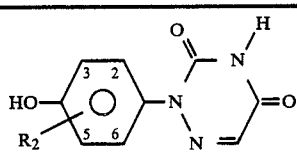

| R$^2$ |
|---|
| 3-Cl |
| 3-CH$_3$ |
| 3,5-Cl |
| 3-CH$_3$, 5-CH$_3$ |

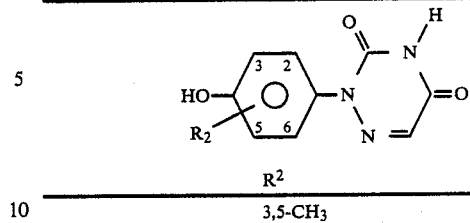

| R$^2$ |
|---|
| 3,5-CH$_3$ |

The substituted heterocycles of the formula III are known or can be prepared analogously to known processes (Beilstein Vol. 27, Katrizky and Rees, Comprehensive Het. Chem. Col. 6 1984).

They have the preferred meanings mentioned further above in the compounds of the formula I. The following compounds of the formula III may be mentioned in detail.

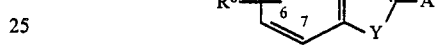

| Y | R$^8$ | A |
|---|---|---|
| S | 6-Cl | Cl |
| S | 5,6-Cl | Cl |
| O | 6-Cl | Cl |
| O | 5,6-Cl | Cl |
| S | 6-Cl | —SO$_2$CH$_3$ |
| S | 5,6-Cl | —SO$_2$CH$_3$ |
| O | 6-Cl | —SO$_2$CH$_3$ |

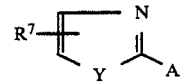

| Y | R$^7$ | A |
|---|---|---|
| S | 4-Cl | Cl |
| S | 4,5-Cl | Cl |
| O | 4-Cl | Cl |
| O | 4,5-Cl | Cl |

The reaction is preferably carried out using diluents.
Suitable diluents are practically all inert organic solvents. These preferably include aliphatic and aromatic, optionally halogenated hydrocarbons, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and dimethyl sulphoxide, tetramethylenesulpones and hexamethylphosphoric triamide.

The reaction is carried out in the presence of inorganic or organic acid acceptors.

Those which may be mentioned are, for example: alkali metal hydroxides such as, for example sodium hydroxide and potassium hydroxide, alkaline earth metal hydroxides such as, for example, calcium hydroxide, alkali metal carbonates and alkoxides such as sodium carbonate and potassium carbonate, sodium methoxide and potassium methoxide, or sodium ethoxide and potassium ethoxide, furthermore aliphatic, aromatic or heterocyclic amines, for example triethylamine, pyridine, 1,5-diazabicyclo-[4,3,0]-non-5-ene (DBN), 1,8-diaza-bicyclo-[5,4,0]-undec-7-ene (DBU) and 1,4-diazabicyclo-[2,2,2]-octane (DABCO).

The reaction takes place at temperatures of between 50° and 200° C., preferably between 80° and 160° C., at atmospheric pressure or elevated pressure. It is preferably carried out at atmospheric pressure.

The process is carried out by combining equimolar amounts of the compounds of the formula II and III in one of the diluents mentioned and heating. After completion of the reaction, the reaction mixture is acidified using dilute inorganic acid (for example hydrochloric acid) and the resulting precipitate is filtered off, washed and dried.

If 2-[4-[2'-benzothiazolyloxy]phenyl]1,2,4-triazine-3,5(2H,4H)-dione is used as the compound of the formula Ia and methyl iodide as the compound of the formula IV in process 2b of the preparation of the compounds of the formula I in which $R^3$ does not stand for hydrogen, then the process can be described by the following equation:

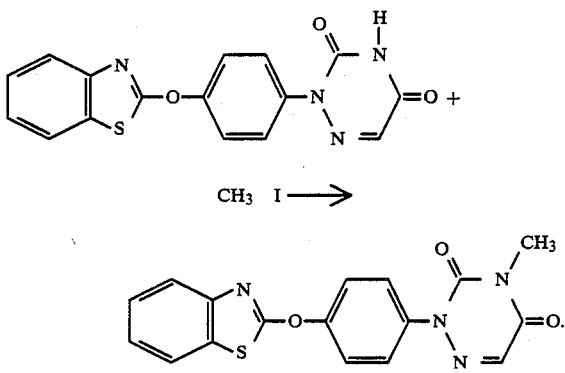

The compounds of the formula Ia are new and are prepared as described in process 2a.

The compounds of the formula IV are known or can be prepared by known methods. Methyl iodide and ethyl bromide may be particularly mentioned.

The process is carried out by reacting a compound of the formula Ia in the presence of a base and a diluent with compounds of the formula IV. All inert organic solvents which are also used for carrying out process Ia can be used as diluents.

The process is carried out in the presence of bases. Preferred bases which may be mentioned are the alkali metal hydroxides such as sodium hydroxide, alkali metal alkoxides such as sodium methoxide or potassium butoxide, metal hydrides such as sodium hydride or organic bases such as 1,8-diazabicyclo[5,40]-undec-7-ene (DBU).

The process is carried out at atmospheric pressure and temperatures of between 20° and 140° C.

The reaction is carried out by combining equimolar amounts of the compound of the formula Ia and base, adding an equimolar amount of the compound of the formula IV to this mixture and heating to the reaction temperature.

If 2-[4-[(2'-benzoxazolylthio)phenyl]-1,2,4-triazine-3,5(2H,4H)-dione is employed as the compound of the formula I in process (2c) for the preparation of the compounds of the formula I having X=SO or $SO_2$, then the process can be described by the following equation:

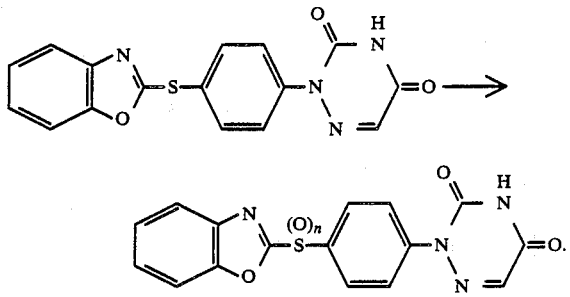

The process is carried out by treating a compound of the formula I having X=S using an oxidant in the presence of a diluent. The following are preferably used as oxidants: hydrogen peroxide and other inorganic peroxides such as sodium peroxide, organic peroxoacids such as, for example, m-chloroperbenzoic acid, and iodine-oxygen compounds such as, for example, sodium metaperiodate.

Diluents which may be preferably employed are alcohols such as, for example, methanol, organic acids such as, for example, acetic acid, and ketones such as acetone, halogenated hydrocarbons such as dichloromethane or acid anhydrides such as acetic anhydride are furthermore used. The oxidation takes place at temperatures of between 0° C. and 120° C. It is preferably carried out under atmospheric pressure.

The amount of oxidant can be varied between one molar and 10 molar. The reaction is carried out by stirring the compounds of the formula I having X=S together with one of the oxidants mentioned for several hours at the reaction temperature mentioned in one of the abovementioned diluents.

If 2-(3-methyl-4-hydroxyphenyl)-1,2,4-triazine-2,5(2H,4H)-dione-6-carboxylic acid is employed as the compound of the formula V in process 4 for the preparation of the compounds of the formula II, then the process can be described by the following equation:

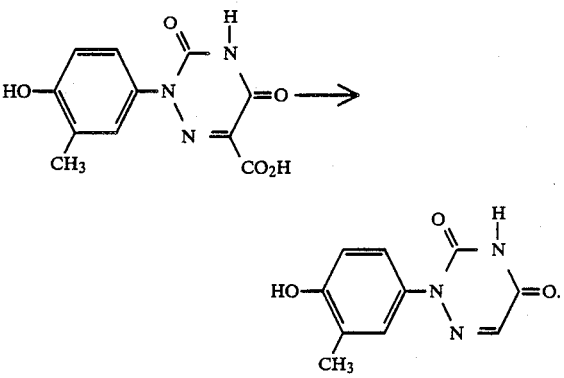

The compound of the formula V in which X stands for O and $R^2$ and $R^3$ stand for hydrogen is known (J. Slouka, C.A. 102, 203946 k).

The compounds of the formula V in which $R^2$ does not stand for hydrogen are new.

The new compounds of the formula V can be prepared analogously to known processes (DE-OS (German Published Specification) No. 2,358,851; J. Slouka, Mh Chem. 96, 124 (1965).

Individual compounds of the formula V which may be mentioned are

| | |
|---|---|
| | structure with HO-phenyl-R² attached to triazine-dione with COOH |
| R² | |
| 3-Cl | |
| 3-CH₃ | |
| 3,5-Cl | |
| 3-CH₃, 5-Cl | |
| 3,5-CH₃ | |

The decarboxylation is optionally carried out in the presence of inert organic diluents. These include aliphatic and aromatic, optionally halogenated hydrocarbons such as nonane, decane, dodecane, xylenes, ethers such as ethylene glycol monobutyl ether and diethylene glycol dibutyl ether, sulfoxides such as dimethylsulfoxide and sulfones such as tetramethylensulfone.

Moreover, the reaction can be carried out in the presence of mercapto group-containing carboxylic acids such as, for example, mercarptoacitic acid orthiosalicylic acid.

The reaction takes place at temperatures of between 150° and 300° C., optionally in the presence of mercapto group-containing carboxylic acids such as, for example, mercapto-acetic acid, preferably between 160° and 250° C., in particular between 180° and 210° C.

The reaction is carried out at atmospheric pressure. The compounds of the formulae V are heated, dissolved or suspended, in substance or in the respective diluent.

If 2-(3-methyl-4-hydroxyphenyl)-6-cyano-1,2,4-triazine 3,5(2H,4H)dione is employed as the compound of the formula VI in process 6 for the preparation of the compounds of the formula V, then the process can be described by the following equation:

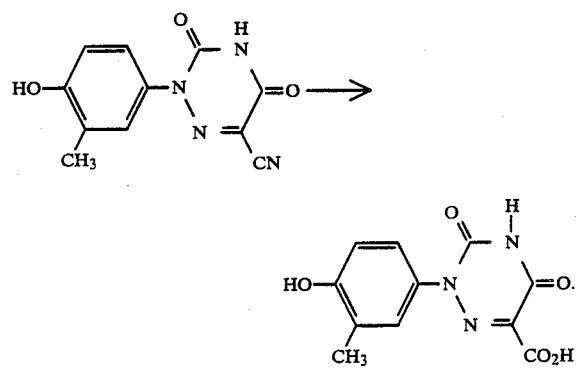

The compound of the formula VI in which X stands for O and R⁴ stands for CN is known (J. Slouka, C.A. 102,203946 K).

The compounds of the formula VI in which R²∼hydrogen are new.

The new compounds of the formula VI can be prepared analogously to known processes (J. Slouka, Mh. Chem. 96, 134 (1965); DOS No. 2,358,851).

Individual compounds of the formula VI which may be mentioned are

| | |
|---|---|
| | structure with HO-phenyl-R₂ attached to triazine-dione with CN |
| R₂ | |
| 3-Cl | |
| 3-CH₃ | |
| 3,5-Cl | |
| 3-CH₃, 5-Cl | |
| 3,5-CH₃ | |

The hydrolysis is carried out under acidic conditions. Those acids which can be used are mineral acids such as, for example, hydrochloric acid, hydrobromic acid, sulphuric acid and mixtures of mineral acids and organic acids such as, for example, acetic acid or propionic acid.

The reaction takes place at temperatures of between 80° and 120° C. It is carried out under atmospheric pressure.

The compounds of the formula VI are dissolved in a 10–30 fold volume of the acid or the acid mixture and heated until conclusion of the hydrolysis.

If ethyl N-[[[cyano(3-methyl-4-hydroxyphenyl)-hydrazinylidene methyl]-carbonyl]-carbamate is employed as the compound of the formula VII in process 8 for the preparation of the compounds of the formula VI, then the process can be described by the following equation:

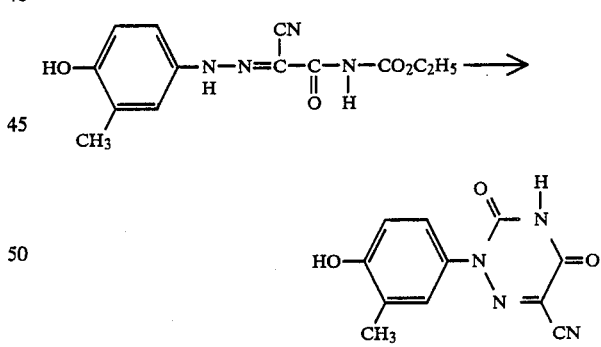

The compounds of the formula VII are new. They can be prepared analogously to known processes (J. Slouka, Mh. Chem. 94, 258 (1963)).

Individual compounds of the formula VII which may be mentioned are

| | | |
|---|---|---|
| | structure HO-phenyl-R²-N-N=C(R⁴)-C(O)-N(H)-COOR⁶ | |
| R² | R⁴ | R⁶ |
| 3-Cl | —CN | —C₂H₅ |

-continued

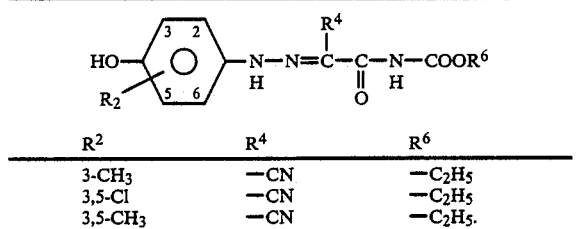

| R² | R⁴ | R⁶ |
|---|---|---|
| 3-CH₃ | —CN | —C₂H₅ |
| 3,5-Cl | —CN | —C₂H₅ |
| 3,5-CH₃ | —CN | —C₂H₅ |

The process is carried out by heating a compound of the formula VII, optionally in the presence of a solvent and a base.

Solvents mentioned in the preparation of the compounds I are used as solvents and bases. Alcohols such as, for example, ethanol or organic acids such as, for example, glacial acetic acid are employed as further particularly preferable organic solvents.

Particularly preferable bases are the hydroxides and acetates of the alkali metals or alkaline earth metals such as, for example, NaOH or sodium and potassium acetate.

The reaction takes place under atmospheric pressure at temperatures of between 70° and 150° C., preferably between 70° and 100° C.

The base used is employed in a molar excess of 10–80 percent. The reaction mixture is preferably acidified using a dilute mineral acid such as, for example, hydrochloric acid after the conclusion of cyclization and the product produced as a solid is filtered off.

If 3-methyl-4-hydroxyaniline is employed as the compound of the formula VIII and ethyl cyanoacetylurethane is employed as the compound of the formula IX in process 10 for the preparation of the compounds of the formula VII, then the process can be described by the following equation:

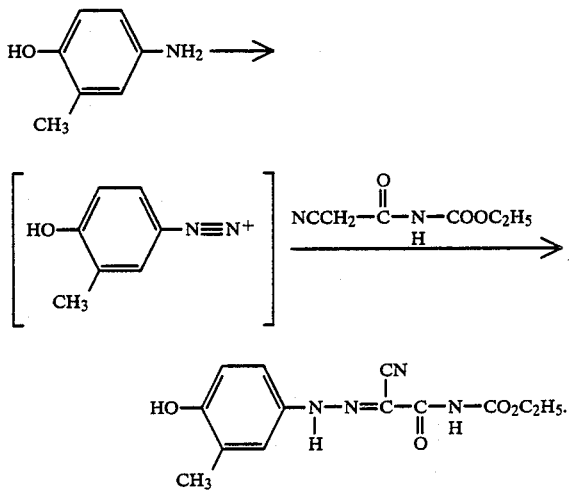

The compounds of the formula VIII and IX are known or can be prepared analogously to known processes.

The process is carried out by reacting an aniline of the formula VIII with NaNO₂ and conc. mineral acid such as, for example, HCl optionally in the presence of diluents. As diluents serve with water miscible diluents such as alcohols, for example, methanol, ethanol, organic acids such as, for example, acetic acid, formic acid, glycolether such as monomethylglycolether, nitriles such as acetonitrile or dimethylsulfoxide.

The diazonium salt thus produced is reacted in situ with a compound of the formula IX such as, for example, malonyldiurethane or cyanoacetylurethane in the presence of a base. Bases used are hydroxides and carbonates of the alkali metals and alkaline earth metals and acetates of sodium, potassium and ammonium.

Furthermore, organic bases such as pyridine or triethylamine can be used.

The diazotization is carried out at atmospheric pressure and at temperatures of between 0° and 10° C. The addition of the compounds of the formula IX takes place at 5° to 20° C. Aniline and nitrite are reacted in equimolar amounts in an excess of acid preferably being 2–3 fold the molar amount. The CH acid compound is added in 0–30% molar excess, preferably 10% excess. The base is added in 1.5–2.5 fold molar excess.

The coupling product of diazonium salt and CH acid compound is insoluble in the reaction medium and can be isolated as a solid.

The process can also be carried out in such a manner that compounds of the formula VI are formed directly without isolation of the compounds of the formula VII. For this purpose the diazotization of the anilines of the formula VIII and the reaction with the urethanes of the formula IX are carried out in a diluent which is suitable for cyclization. When diazotization and coupling have been carried out the reaction mixture is heated and the Triazinedione of the formula VI is isolated.

The following may be mentioned as diluents: alcohols such as methanol and ethanol.

Cyclization is carried out by heating the reaction mixture to about 80° to 120° C., preferably about 80° to 100° C.

Working up is carried out as described further above for the preparation of the compounds of the formula VI. The active compounds are suitable for combating parasitic protozoa which occur in animal rearing and animal breeding with productive, breeding, zoo, laboratory, experimental and pet animals and have favorable toxicity to warm blooded animals. They are active against all or individual stages of development of the pests and against resistant and normally sensitive strains. By combating the parasitic protozoa, disease, cases of death and yield reductions (for example in the production of meat, milk, wool, hides, eggs, honey etc.) are lowered so that more economical and simpler animal production is possible by the use of the active compounds.

The parasitic protozoa include:
Mastigophora (Flagellata) such as, for example, *Trypanosomatidae*, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica,* such as, for example, Trichomonadidae, for example, *Giardia lamblia, G. canis.* Sarcomastigophora (Rhizopoda) such as, Entamoebidae, for example *Entamoeba histolytica,* Hartmanellidae, for example, Acanthamoeba sp., Hartmanella sp.

Apicomplexa (Sporozoa) such as Eimeridae, for example, *Eimeria acervulina, E. adenoides, E. alabahmensis, E. anatis, E. anseris, E. arloingi, E. ashata, E. auburnensis, E. bovis, E. brunetti, E. canis, E. chinchillae, E. clupearum, E. columbae, E. contorta, E. crandalis, E. dabliecki, E. dispersa, E. ellipsoidales, E. falciformis, E. faurei, E. flavescens, E. gallopavonis, E. hagani, E. intesti-*

*nalis, E. iroquoina, E. irresidua, E. labbeana, E. leucarti, E. magna, E. maxima. E. media, E. meleagridis, E. meleagrimitis, E. mitis, E. necatrix, E. ninakohlyakimovae, E. ovis, E. parva, E. pavonis, E. perforans, E. phasani. E. piriformis, E. praecox, E. residua, E. scabra, E. spec., E. stiedai, E. suis, E. tenella, E. truncata, E. truttae, E. zuernii, Globidium spec., Isospora belli, I. canis, I. felis, I. ohioensis, I. rivolta,* I. spec., *I. suis, cystisospora* spec., Cryptosporidium spec. such as Toxoplasmadidae, for example, *Toxoplasma gondii,* such as Sarcocystidae, for example, *Sarcocystis bovicanis, S. bovihominis, S. ovicanis, S. ovifelis,* S. spec., *S. suihominis* such as Leucozoidae, for example, *Leucozytozoon simondi,* such as Plasmodiida, for example, *Plasmodium berghei, P. falciparum, P. malariae, P. ovale, P. vivax,* P. spec., such as Piroplasmea, for example, *Babesia argentina,* B. bovis, B. canis, B. spec., *Theileria parva,* Theileria spec., such as Adeleina, for example, *Hepatozoon canis,* H spec.

Furthermore Myxospora and Microspora, for example, Glugea spec. Nosema spec. Furthermore *Pneumocystis carinii,* and also Ciliophora (Ciliata) such as, for example, *Balantidium coli,* Ichthiophthirius spec., Trichodina spec., Epistylis spec.

Moreover, the compounds according to the invention are active against various fish parasites belonging to the helminths (worms) above all sucking worms (Trematoda, Monogenea) such as, for example, Gyrodactylus spec., Dartylogyrus spec., Pseudodatylogyrus spec., Diplozoon spec.

The productive and breeding animals include mammals such as, for example, cattle, horses, sheep, pigs, goats, camels, water buffaloes, donkeys, rabbits, fallowdeer, reindeer and pelt animals such as, for example, mink, chinchilla, racoon, birds such as, for example, chickens, geese, turkeys, ducks, doves and species of bird for domestic and zoo rearing. Commercial and ornamental fish are furthermore included.

The laboratory and experimental animals include mice, rats, guinea-pigs, golden hamsters, dogs and cats.

The pet animals include dogs and cats.

Administration can take place both prophylactically and therapeutically.

Administration of the active compounds takes place enterally, parenterally, dermally for nasally, directly or in the form of suitable preparations.

Enteral administration of the active compounds takes place, for example, orally in the form of powders, suppositories, tablets, capsules, pastes, drinks, granules, drenches, boli, medicated feed or drinking water. Dermal administration takes place, for example, in the form of dipping, spraying, bathing, washing, pouring-on and spotting-on and dusting. Parenteral administration takes place, for example, in the form of injections (intramuscular, subcutaneous, intravenous, intraperitoneal) or by implants.

Suitable preparations are as follows:

Solutions such as solutions for injection, oral solutions, concentrates for oral administration after dilution, solutions for use on the skin or in body cavities, pouring-on formulations and gels;

Emulsions and suspension for oral or dermal administration and for injection; semi-solid preparations;

Formulations in which the active compound is processed in an ointment base or in an oil-in-water or water-in-oil emulsion base;

Solid preparations such as powders, premixes or concentrates, granules, pellets, tablets, boli and capsules; aerosols and inhalants, and active-compound-containing molded articles.

Solutions for injection are administered intravenously, intramuscularly and subcutaneously.

Solutions for injection are prepared by dissolving the active compound in a suitable solvent and adding, if necessary, additives such as solubilizers, acids, bases, buffer salts, antioxidants and preservatives. The solutions are sterile-filtered and filled. Solvents which may be mentioned are as follows:

Physiologically tolerable solvents such as water, alcohols such as ethanol, butanol, benzyl alcohol and glycerol, hydrocarbons, propylene glycol, polyethylene glycols, N-methylpyrrolidone, and mixtures thereof.

The active compounds can optionally also be dissolved in physiologically tolerable vegetable or synthetic oils which are suitable for injection.

Solubilizers which may be mentioned are solvents which promote the solution of the active compound in the main solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are administered directly. Concentrates are administered orally after previous dilution to the administration concentration. Oral solutions and concentrates are prepared as described above in the solutions for injection, it being possible to dispense with sterile working.

Solutions for use on the skin are poured on, spread on, rubbed in, sprayed on, sprinkled on or applied by dipping, bathing or washing. These solutions are prepared as described above in the solutions for injection.

It can be advantageous to add thickeners in the preparation. Thickeners are inorganic thickeners such as bentonites, colloidal silica and aluminium monostearate, organic thickeners such as cellulose derivatives, polyvinyl alcohols and their copolymers, acrylates and methacrylates.

Gels are applied to or spread on the skin or introduced into body cavities. Gels are prepared by adding sufficient thickener to solutions, which have been prepared as described in the solutions for injection, that a clear material with a ointment-like consistency results. The thickeners mentioned further above are employed as thickeners.

Pouring-on formulations are poured on or sprayed on to limited regions of the skin, by means of which the active compound either penetrates the skin and acts systemically or is distributed over the body surface.

Pouring-on formulations are prepared by dissolving, suspending or emulsifying the active compound in suitable skin-compatible solvents or solvent mixtures. Further auxiliaries such as colourants, absorption-promoting substances, antioxidants, light screens and adhesives are optionally added.

Solvents which may be mentioned are water, alkanols, glycols, polyethylene glycols, polypropylene glycols, glycerol, aromatic alcohols such as benzyl alcohol, phenyl ethanol, phenoxy ethanol, esters such as ethyl acetate, butyl acetate and benzyl benzoate, ethers such as alkylene glycol alkyl ethers such as dipropylene glycol monomethyl ether and diethylene glycol monobutyl ether, ketones such as acetone, methyl ethyl ketone, aromatic and/or aliphatic hydrocarbons, vegetable or synthetic oils, DMF, dimethylacetamide, N- methylpyrrolidone or 2-dimethyl-4-oxy-methylene-1,3-dioxolane.

Colorants are all colorants, which can be dissolved or suspended, permitted for use in animals.

Absorption-promoting substances are, for example, DMSO, spreading oils such as isopropyl myristate, dipropylene glycol pelargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Light screens are, for example, substances from the benzophenone or novantisolic acid class.

Adhesives are, for example, cellulose derivatives, starch derivatives, polyacrylates, natural polymers such as alginates, or gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing these with the solvent of the other phase with the aid of suitable emulsifiers and, if appropriate, further auxiliaries such as colorants absorption-promoting substances, preservatives, antioxidants, light screens and viscosity-raising substances.

Hydrophobic phases (oils) which may be mentioned are paraffin oils, silicone oils, natural vegetable oils such as sesame oil, almond oil, castor oil, synthetic triglycerides such as caprylic/capric acid biglyceride, a triglyceride mixture with vegetable fatty acids of chain length $C_{8-12}$ or other specially selected natural fatty acids, partial glyceride mixtures of saturated or unsaturated fatty acids, if necessary also containing hydroxyl groups, or mono- and diglycerides of the $C_8/C_{10}$-fatty acids.

Fatty acid esters such as ethyl stearate, di-n-butyryl adipate, hexyl laurate, dipropylene glycol pelargonate, esters of a branched fatty acid of average chain length containing saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, wax-like fatty acid esters such as dibutyl phthalate, diisopropyl adipate, and ester mixtures related to the latter, inter alia fatty alcohols such as isotridecyl alcohol, 2-octyldodecanol, cetyl stearyl alcohol and oleyl alcohol.

Fatty acids such as, for example, oleic acid and its mixtures.

Hydrophilic phases which may be mentioned are water, alcohols such as, for example, propylene glycol, glycerol, sorbitol and their mixtures.

Emulsifiers which may be mentioned are non-ionic surfactants, for example, polyoxyethylated castor oil, polyoxyethylated sorbitan monooleate, sorbitan monostearate, glycerol monostearate, polyoxyethyl stearate and alkylphenol polyglycol ethers; ampholytic surfactants such as di-Na N-lauryl-$\beta$-iminodipropionate or lecithin; anion-active surfactants, such as Na lauryl sulphate, fatty alcohol ether sulphates and mono/dialkyl polyglycol ether orthophosphoric acid ester monoethanolamine salt; cation-active surfactants such as cetyltrimethylammonium chloride.

Further auxiliaries which may be mentioned are viscosity-raising and emulsion-stabilizing substances such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions can be administered orally, dermally or as injections. They are prepared by suspending the active compound in an excipient liquid, if appropriate with the addition of further auxiliaries such as wetting agents, colorants, absorption-promoting substances, preservatives, antioxidants or light screens.

Excipient liquids which may be mentioned are all homogenous solvents and solvent mixtures.

Wetting agents (dispersing agents) which may be mentioned are the surfactants mentioned further above.

Further auxiliaries which may be mentioned are those mentioned further above.

Semi-solid preparations may be administered orally or dermally. They differ from the suspensions and emulsions described above only by their higher viscosity.

To prepare solid preparations, the active compound is mixed with suitable excipients, if appropriate with the addition of auxiliaries, and brought into the desired form.

Excipients which may be mentioned are all physiologically tolerable solid inert substances. Those which may be used are inorganic and organic substances. Inorganic substances are, for example, sodium chloride, carbonates such as calcium carbonate, hydrogen carbonate, aluminas, silicas, clays, precipitated or colloidal silica and phosphates.

Organic substances are, for example, sugar, cellulose, foodstuffs and feedstuffs such as milk powder, animal meals, cereal meals and shreds and starches.

Auxiliaries are preservatives, antioxidants and colorants which have already been mentioned further above.

Further suitable auxiliaries are lubricants and glidants such as, for example, magnesium stearate, stearic acid, talc, bentonite, disintegration-promoting substances such as starch or cross-linked polyvinylpyrrolidone, binders such as, for example, starch, gelatin or linear polyvinylpyrrolidone and dry binders such as microcrystalline cellulose.

The active compounds may also be present in the preparations mixed with synergists or with other active compounds.

Ready-to-use preparations contain the active compound in concentrations of 10 ppm–20 percent by weight, preferably 0.1–10 percent by weight.

Preparations which are diluted before administration contain the active compound in concentrations of 0.5–90 percent by weight, preferably 1 to 50 percent by weight.

In general, it has proved advantageous to administer amounts of about 0.5 to about 50 mg, preferably 1 to 20 mg, of active compound per kg of body weight per day to obtain effective results.

The active compounds may also be administered with the feed or drinking water of the animals.

Feedstuffs and foodstuffs contain 0.01 to 100 ppm, preferably 0.5 to 50 ppm, of the active compound in combination with a suitable edible material.

Such a feedstuff and foodstuff can be used both for curative purposes and for prophylactic purposes.

The preparation of such a feedstuff or foodstuff takes place by mixing a concentrate or a premix, which contains 0.5 to 30%, preferably 1 to 20% by weight of an active compound mixed with an edible organic or inorganic excipient, with customary feedstuffs. Edible excipients are, for example, corn meal or corn and soyabean meal or mineral salts which preferably contain a low amount of an edible dust prevention oil, for example, corn oil or soya oil. The premix obtained in this case can then be added to the complete feedstuff before it is fed to the animals.

Examples of employment in coccidiosis which may be mentioned are:

For the cure and prophylaxis, for example, of coccidiosis in poultry, in particular in chickens, ducks, geese and turkeys, 0.1 to 100 ppm, preferably 0.5 to 100 ppm, of an active compound are mixed with a suitable edible material, for example, a nutritive feedstuff. If desired, these amounts may be increased, particularly when the active compound is well tolerated by the receiver. Correspondingly, administration may take place via the drinking water.

For the treatment of individual animals, for example, in the case of the treatment of coccidiosis in mammals or toxoplasmosis, active compound amounts of 0.5 to 100 mg/kg of body weight are preferably administered daily, in order to obtain the desired results. In spite of this, it may be temporarily necessary to deviate from the amounts mentioned, in particular depending on the body weight of the test animal or the type of administration method, but also on account of the animal order and its individual reaction to the active compound or the type of formulation and the time or the interval at which it is administered. Thus, in certain cases it may be sufficient to manage with less than the previously mentioned minimum amount, whereas in other cases the upper limit mentioned must be exceeded. In the administration of larger amounts, it can be expedient to divide these into several individual administrations within the course of the day.

EXAMPLE A

Coccidiosis in chickens 9 to 11 day old chicks were infected with 40,000 sporulated oocysts from strongly virulent strains of Eiveria acervulina, E. maxima and E. tenella, the disease pathogens of intestinal coccidiosis.

3 days before infection and 8 days after infection (end of the test), active compound was administered mixed in the feed of the animals in the concentrations indicated.

The number of oocysts in the faeces was determined with the aid of the McMaster Chamber (see Engelbrecht and coworkers "Parasitologische Arbeitsmehoden in Medizin and Veterinärmedizin", ("Parasitological working methods in medicine and veterinary medicine"), p. 172, Academie-Verlag, Berlin (1965)).

Those doses which prevented, completely or to a large extent, the excretion of oocysts and/or clinical symptoms of coccidiosis, including mortality, are regarded as effective. The effective doses are indicated in the following table:

TABLE 1

| | | | Coccidiosis in chickens | | |
|---|---|---|---|---|---|
| Example No. | Dose ppm. | Death rate dead/used | Oocyst excretion in % in comparison to untreated infected control | Increase in weight in % in comparison to non-infected untreated control | Blood excretion with the faeces |
| Untreated infected control | | 2/6 | 100 | 35 | heavy |
| 4 | 50 | 0/3 | 0 | 100 | none |
| | 25 | 0/3 | 0 | 100 | none |
| | 10 | 0/6 | 0 | 100 | none |

PREPARATION EXAMPLES

I. Examples of process 2a

Example 1

2-[4[4'Chloro)-2'-thiazolyloxy]phenyl]-3,5(2H,4H)-dioxo-as-triazine

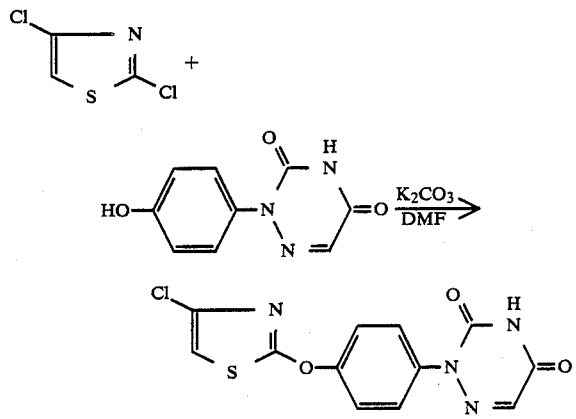

29 (0.01 mol) of hydroxyphenylazuracil, 1.5 g (0.01 mol) of dichlorothiazole and 1.4 g (0.01 mol) of potassium carbonate are stirred under reflux for 2 hours in 20 ml of dry DMF. The cooled reaction mixture is acidified using HCl and precipitated product is filtered off with suction. After recrystallizing from ethanol, 2.9 g (90% of theory) of thiazolyloxyarylazaurazil are obtained.

The following are prepared analogously:

EXAMPLE 2

2-[-[(4'-Chloro-5'-methyl)-2'-thiazolyloxy]phenyl]1,2,4-triazine-3,5(2H,4H)dione.

EXAMPLE 3

2-(4-(2-benzothiazolyloxy)-phenyl)-1,2,4-triazine-3,5(2H,-4H)-dione.

Example 4

2-[4[6'-Chloro)2'-benzothiazolyloxy]-3,5-dichlorophenyl]-1,2,4-triazine-3,5-(2H,4H)dione.

II. Example of process 2b

Example 5

2-[4-[(4'-Chloro)-2'-thiazolyloxy]phenyl]-3-N-methyl-3,5-(2H,4H)-dioxo-1,2,4-triazine

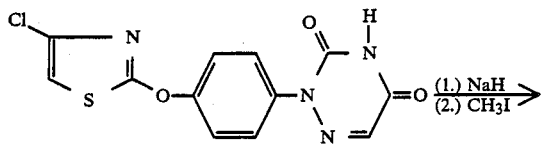

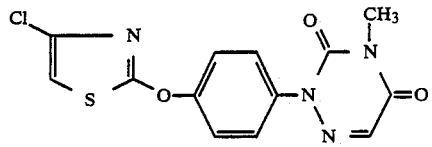

2 g (6 mmol) of thiazolyloxyarylazauracil are dissolved in 20 ml of absolute DMSO and 0.14 g (6 mmol) of sodium hydride is added. The mixture is stirred for 20 min. at RT and 1.3 g (9 mmol) of methyl iodide in 5 ml of DMSO are then added under argon. The mixture is warmed to 50° C. and held at this temperature for 3h. Subsequently, the reaction mixture is concentrated in vacuo and water is then added. After filtering off the precipitated solid with suction, 1.5 g (71% of theory) of the N-methyl compound are thus obtained.

Examples of process 2c

2-[4-[6'-Chloro)2'-benzoxazolylsulphoxyl]-3,5-dichlorophenyl]1,2,4-triazine-3,5(2H,4H)dione.

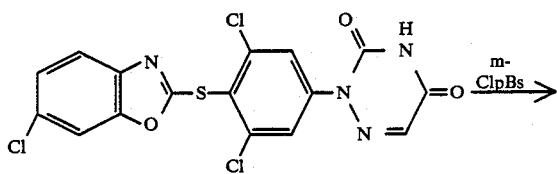

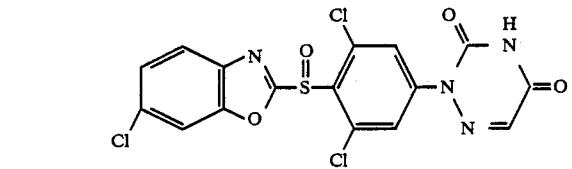

10 g (0.027 mol) of chlorobenzoxazolylthiophenylazauracil are dissolved in a mixture of 200 ml of methanol and 100 ml of dichloromethane. The mixture is cooled to 10° C. and 4.6 g of m-chloroperbenzoic acid (85% strength) are added at this temperature. After stirring for 10 h at 10° C., the solvent is stripped off in vacuo and the residue is recrystallized from isopropanol. 8.5 g (82% of theory) of sulphoxide are thus obtained.

The following are prepared analogously:

Example 6

2-[4-(2'-Benzoxazolylsulphoxyl)-3,5-dichlorophenyl]1,2,4-triazine-3,5(2H,4H)dione Example 7

2-[4-(2'-Benzoxazolylsulphoxyl)-3,5-dichlorophenyl]1,2,4-triazine-1,2,4-triazine-3,5(2H,4H)dione.

Example 8

2-[4-[(6'-Chloro)-2'-benzoxazolylsulphonyl]-3,5-dichlorophenyl]1,2,4-triazine-3,5(2H,4H)dione.

8.8 g (0.02 mol) of chlorobenzoxazolylthiophenylazauracil are dissolved in 100 ml of glacial acetic acid and stirred for 18 h under reflux with 40 ml of 30% strength hydrogen peroxide. After cooling, water is added and the precipitate deposited is filtered off with suction. Recrystallization from isopropanol yields 6.9 g of sulphone (73% of theory).

The following are prepared analogously:

Example 9

2-[4-(2'-Benzoxazolylsulphonyl)-3,5-dichlorophenyl]1,2,4-triazine-3,5(2H,4H)dione.

Example 10

2-[4-(2'-Benzoxazolylsulphonyl)-phenyl]1,2,4-triazine-3,5(2H,4H)dione.

III. Example of process 4

IIIa
2-(4-Hydroxyphenyl)-1,2,4-triazine-3,5(2,4H)dione

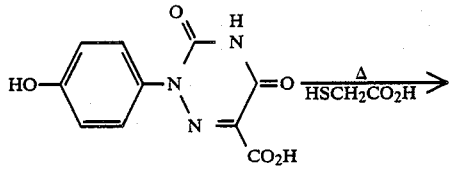

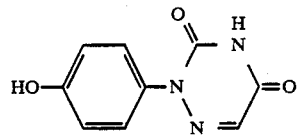

34 g (0.137 mol) of carboxylic acid are heated to 170° C. in 34 ml of mercaptoacetic acid. After 1.5 h, the mixture is allowed to cool, water is added and 24 g (82% of theory) of decarboxylated product are obtained after filtering off.

The following are prepared analogously.

IIIb
2-(3,5-Dichloro-4-hydroxyphenyl)-1,2,4-triazine-3,5-(2H,4H)dione

IIIc
2-(3-Methyl-4-hydroxyphenyl)-1,2,4-triazine-3,5(2H,4H)-dione

IIId
2-(4-Hydroxyphenyl)-3,5-(2H,4H)dione-1,2,4-triazine

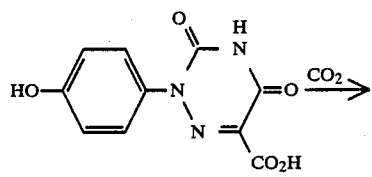

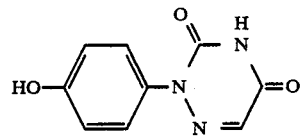

19 g (0.076 mol) of carboxylic acid are heated under argon in a metal bath at 260°–280° C. until completion of gas evolution. After cooling, the residue is recrystallized from ethanol. 10 g (64% of theory) of azauracil result.

IV Examples of process 6

IVa
2-(4-Hydroxyphenyl)-3,5(2H,4H)dioxo-1,2,4-triazine-6-carboxylic acid

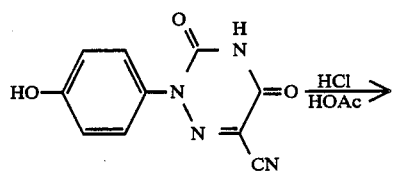

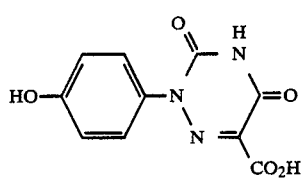

30.1 (0.13 mol) of cyanoazauracil are stirred under reflux for 14 h in 1,000 ml of HCl/glacial acetic acid (1:1). After cooling, the mixture is concentrated, water is added to the residue and the precipitated product is filtered off with suction. 19 g (59% of theory).

The following are prepared analogously
IVb
2-(3,5-Dichloro-4-hydroxyphenyl)-1,2,4-triazine-3,5-(2H,4H)dione-6-carboxylic acid
IVc
2-(3-Methyl-4-hydroxyphenyl)-1,2,4-triazine-3,5-(2H,4H)-dione-6-carboxylic acid V Examples of process 8

Va
2-(4-Hydroxyphenyl)-3,5-(2H,4H),dioxo-6-cyano-1,2,4-triazine

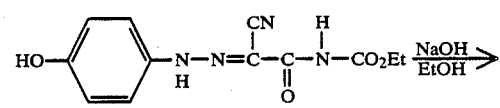

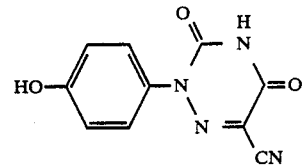

43.8 g (0.158 mol) of the hydrazonocyanourethane and 8.5 g (0.213 mol) of NaOH are heated under reflux for 2 h in 400 ml of abs. ethanol. The mixture is subsequently cooled, acidified using hydrochloric acid and concentrated in vacuo. The residue is stirred with water and the deposited precipitate is filtered off with suction. 30.1 g (85% of theory) of cyanoazauracil are thus obtained after drying.
Vb
2-(3,5-Dichloro-4-hydroxyphenyl)-6-cyano-1,2,4-triazine-3,5(2H,4H)dione
Vc
2-(3-Methyl-4-hydroxyphenyl)-6-cyano-1,2,4-triazine.

VI Examples of process 10

VIa
Ethyl N-[[[Cyano(4-hydroxyphenyl)-hydrazinylidene]-methyl]carbonyl]-carbamate

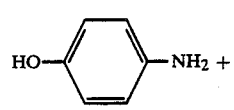

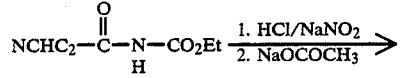

10 g (0.091 mol) of 4-hydroxyaniline are dissolved in 19.7 ml of conc. HCl and 200 ml of glacial acetic acid and a solution of 6.4 g (0.092 mol) of sodium nitrite in 30 ml of water is added dropwise at 0°–5° C. The mixture is stirred until a clear solution is formed, then a mixture of 14.3 g (0.092 mol) of cyanoacetylurethane and 21 g (0.25 mol) of sodium acetate is added and the mixture is stirred for 3 h at 10° C. The reaction mixture is concentrated in vacuo, the residue is stirred with water and the solid is filtered off with suction. 19 g (75%) of product are thus obtained as a fine crystalline yellow powder.

The following are prepared analogously.
VIb
Ethyl N-[[[-cyano(3,5-dichloro-4-hydroxyphenyl)-hydrazinylidene]methyl]carbonyl]-carbamate.
VIc
Ethyl N-[[[cyano(3-methyl-4-hydroxyphenyl)-hydrazinylidene]methyl]carbonyl]-carbamate.
VId
2-(3,5-Dichloro-4-hydroxyphenyl)-1,2,4-triazine-3,5 (2,4H)-dione

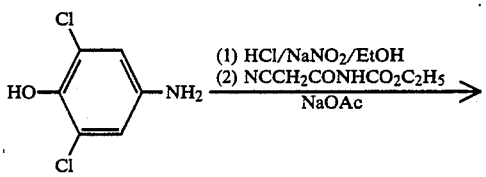

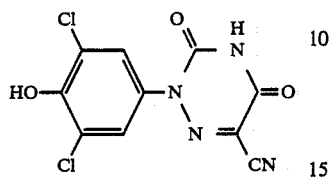

196 g (1.1 mole) of 2,6-dichloro-4-aminophenol are dissolved in 2.4 l of ethanol and 240 ml conc. hydrochloric acid. To this solution cooled to 6° to 10° C., an equimolar amount of aqueous sodium nitrite solution is added slowly. The mixture is subsequently stirred for 30 minutes and then 400 g sodium acetate and 172 g (1.1 mole) cyanoacetylurethane are added in succession and the mixture is subsequently stirred for 1 hour at room temperature. Then it is heated for 2 hours under reflux and cooled and water is added. The precipitate deposited is filtered off with suction and washed with dilute HCl and water, 289 g (88% of theory) of cyanazauracil are thus obtained.

It will be appreciated that the instant specification and claims are set forth by way of illustration and not limitation, and that various modifications and changes may be made without departing from the spirit and scope of the present invention.

What is claimed is:

1. A compound of the formula II

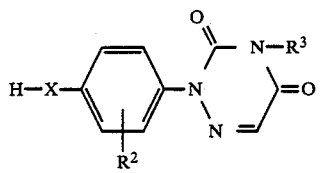

in which
X stands for O or S,
$R^2$ stands for one or more, identical or different radicals selected from the group consisting of halogen, nitro, alkyl, alkoxy, alkylthio, halogenoalkyl, halogenoalkoxy, halogenoalkylthio and for the case in which X stands for S, $R^2$ additionally stands for hydrogen,
$R^3$ stands for hydrogen, alkyl, alkenyl, alkinyl or aralkyl.

2. A compound of the formula V

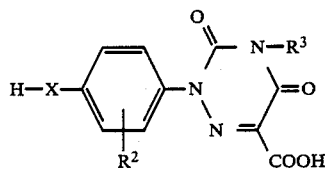

in which
X stands for O or S,
$R^2$ stands for one or more, identical or different radicals selected from the group consisting of halogen, nitro, alkyl, alkoxy halogenoalkyl and halogenoalkoxy and for the case in which X stands for S, additionally for hydrogen,
$R^3$ stands for hydrogen, alkyl, alkenyl, alkinyl or aralkyl.

3. A compound of the formula VI

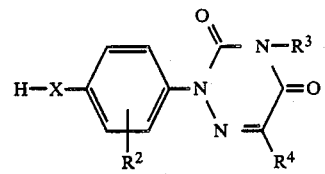

in which
X stands for O or S,
$R^2$ stands for one or more, identical or different radicals selected from the group consisting of halogen, nitro, alkyl, alkoxy, alkylthio, halogenoalkyl, halogenoalkoxy and halogenoalkylthio and for the case in which X stands for S, $R^2$ additionally stands for hydrogen,
$R^3$ stands for hydrogen, alkyl, alkenyl, alkinyl or aralkyl and
$R^4$ stands for the radicals —CN or

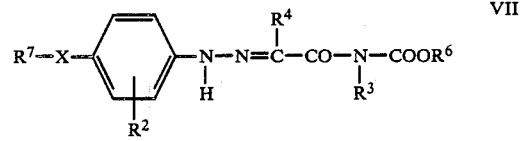

wherein $R^5$ stands for unsubstituted or substituted alkyl or aryl.

4. A compound of the formula VII

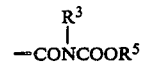

in which
X stands for O or S,
$R^2$ stands for one or more, identical or different radicals selected from the group consisting of halogen, nitro, alkyl, alkoxy, alkylthio, halogenoalkyl, halogenoalkoxy and halogenoalkylthio and for the case in which X stands for S,
$R^2$ additionally stands for hydrogen,
$R^3$ stands for hydrogen, alkyl, alkenyl, alkinyl or aralkyl,
$R^4$ stands for the radicals -CN or

$R^5$ stands for unsubstituted or substituted alkyl or aryl,
$R^6$ stands for alkyl or unsubstituted or substituted aryl,
$R^7$ stands for hydrogen or unsubstituted or substituted

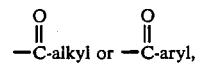

and for the case in which $R^7$ stands for hydrogen or X stands for S, $R^2$ can additionally stand for hydrogen.

* * * * *

UNITED STATES PATENT AND TRADEMARK OFFICE
CERTIFICATE OF CORRECTION

PATENT NO. : 4,968,795

DATED : November 6, 1990

INVENTOR(S) : Lindner et al.

It is certified that error appears in the above-identified patent and that said Letters Patent is hereby corrected as shown below:

Col. 26, lines 24-30   After " or " insert -- $-\text{CONCOOR}^5$-- and delete

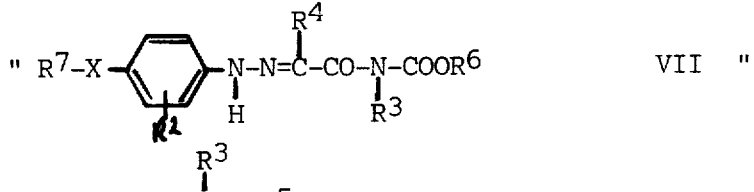

Col. 26, line 38   Delete " $-\text{CONCOOR}^5$ " and substitute

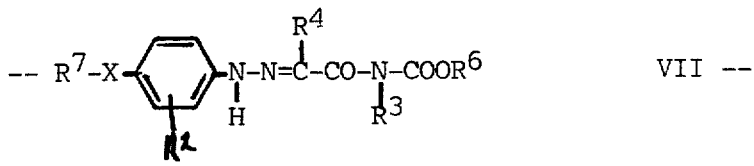

Signed and Sealed this

Sixth Day of October, 1992

Attest:

DOUGLAS B. COMER

Attesting Officer      Acting Commissioner of Patents and Trademarks